United States Patent [19]

Hamilton et al.

[11] 4,120,196
[45] Oct. 17, 1978

[54] PRODUCTION TOOL WEAR DETECTOR

[75] Inventors: Dean Elwyn Hamilton, Lancaster, Mass.; Marcel Pierre Joseph Gaudreau, La Pocatiere, Canada; Alan Leo Wu, Cambridge, Mass.

[73] Assignee: The Charles Stark Draper Laboratory, Inc., Cambridge, Mass.

[21] Appl. No.: 781,145

[22] Filed: Mar. 25, 1977

[51] Int. Cl.$^2$ .............................................. G01N 3/58
[52] U.S. Cl. ..................................... 73/104; 33/174 L
[58] Field of Search ............... 73/7, 104, 162, 37.5, 73/37.6; 340/267 R; 324/34 PS, 34 GT; 33/174 L

[56] References Cited

U.S. PATENT DOCUMENTS

| | | | |
|---|---|---|---|
| 3,522,524 | 8/1970 | Smith et al. | 73/162 X |
| 3,641,431 | 2/1972 | Pigage et al. | 33/174 L X |
| 3,851,323 | 11/1974 | Eltgen | 340/267 R |
| 3,895,446 | 7/1975 | Orlov et al. | 33/174 L |
| 3,987,670 | 10/1976 | Tuzzeo et al. | 73/104 |

Primary Examiner—Charles A. Ruehl
Attorney, Agent, or Firm—Robert F. O'Connell

[57] ABSTRACT

A production tool wear detector which provides a direct, non-contact measurement of the amount of material removed from a cutting tool due to wear during operation thereof. One or more sensing devices monitor the distance to a selected wearing cutting surface of the tool and the distance to a selected non-wearing reference surface of the tool and such distances are suitably processed by appropriate electronic circuitry so as to provide a signal representing the wear characteristics of such cutting surface, which signal can be appropriately displayed, or otherwise used, to make an operator aware of when the tool has worn to a point below a selected threshold. Such a system permits in situ, continuous monitoring of one or more cutting tools during actual use of the tools in a consistent and accurate fashion at relatively low cost.

23 Claims, 12 Drawing Figures

PRODUCTION TOOL WEAR DETECTOR

INTRODUCTION

This invention relates generally to the detection of tool year and, more particularly, to a method and apparatus for providing a direct measurement of tool wear which is especially useful for tools used in production line operation.

BACKGROUND OF THE INVENTION

It is desirable that tools, such as are used on production lines, be permitted to be used until their useful life is ended, that is, until the work-piece which is being produced thereby no longer meets the production tolerances and quality control standards therefor. Once the tool has reached the end of its useful life, it should be changed and replaced by a new tool and, if feasible, the used tool can be re-sharpened for subsequent re-use.

Production costs can be substantially affected by the policy adopted by a manufacturer in changing tools as a result of wear. For example, if a tool is changed before it is worn, higher tool replacement costs and re-sharpening costs result. Further, costs are increased by the excessive down time caused by too frequent tool changes. On the other hand, if tools are not changed when they reach the end of their useful life, parts which no longer meet the production tolerances and quality control standards may be produced or an increased amount of tool breakage may occur.

In order to optimize a tool changing policy, it is desirable to devise a method which calls for an appropriate change of all tools before or as near as possible at the end of their useful lives. Methods which have been suggested up to now have not always been able to meet such a criterion or, in some cases, even to approach it effectively. Tool change policies up to now have often been based merely on the use of essentially fixed, periodic changes thereof, normally not determined by the actual wear of the tools. Thus, it has been suggested that some tools be changed regularly over a specified time period or after a selected number of work pieces have been produced thereby. However, due to a plurality of variables, such as the hardness of the work piece and the cutting conditions under which the tool operates, the life of a tool tends to be random in nature with standard deviations as large as one-half of the average values. As a result, under such procedures, many tools are changed before they reach the end of their useful life while other tools continue to be used beyond their useful lives.

Other procedures attempt to measure the wear characteristics of tools in some appropriate manner as by the use of indirect analyses of tool characteristics not specifically reflecting the actual wear characteristics of the tool itself. A summary of state-of-the-art techniques for sensing tool wear can be found in the publication, "Survey of the State of the Art of Tool Wear Sensing Techniques", by N. Cook et al., available from the Materials Processing Laboratory, Department of Mechanical Engineering, Massachusetts Institute of Technology, Cambridge, Massachusetts, September 1975 and prepared under National Science Grant No. GI-43861.

The conclusion reached in the above survey is that present day techniques are inadequate to fill the needs of manufacturers, particularly where on-line techniques are required to obtain reliable tool wear information for tools having relatively complex geometries, such as for milling cutters and twist drills. The use of cutting process parameters, such as cutting forces, power consumption, cutting edge temperature, or machine vibrations, is unreliable because of the variations therein caused by variations in work-piece hardness and in cutting conditions which make it difficult to identify tool wear therefrom. Other more direct methods measure the dimensions of the wear zone in various manners using micrometers, profile tracers, weight measurements, and ultrasonic, optical or pneumatic techniques. Such methods prove difficult or impractical to implement in production line contexts and the accuracies thereof are often highly questionable. Moreover, since the dimensions of the wear zone are very small, it is difficult to obtain on-line measurements thereof in typical practical environments.

It is desirable that a reliable tool wear measurement technique be available and adaptable to production line use, the implementation thereof being capable of being embodied in a configuration which is compact, rigid and relatively insensitive to the environment and that such technique and apparatus be relatively easy to use and available at a reasonable cost.

BRIEF SUMMARY OF THE INVENTION

This invention utilizes a method and apparatus which permits a direct non-contact measurement of the amount of material which is removed from a cutting tool due to wear during the operation thereof and which provides a definite and reliable measurement of tool wear at a reasonable cost so that the changing of tools at an optimum point in terms of their useful lives can be accomplished.

In accordance therewith, sensing means are mounted ajacent a tool or tools which are to be monitored so that the sensing means can measure one distance which is representative of a selected dimension of the cutting or wearing surface of the tool and can measure at least one other distance which is representative of at least one selected dimension of a non-wearing reference surface of to tool. Means are provided for comparing the difference between such distances, the comparison representing the amount of tool wear which has occured at the cutting surface. The difference between the distances can be appropriately displayed, as on an oscilloscope or a meter, to indicate the wear profile or percentage of wear of the cutting surface which has occured. When the cutting surface has worn to a point below a selected threshold, an appropriate visual or audible indication thereof is provided so that the tool can be removed and a new tool inserted therefor.

The method and apparatus of the invention permits a continuous monitoring of tool wear in a consistent and accurate fashion, which method and apparatus can be implemented at relatively low cost. Further, the direct, non-contact measurement of the current surface wear, can be performed while the tool is in operation, as on a production line, the output of the tool wear detection system being displayed in either graphical form or in a discrete form or in the form of a discrete signal which can either actuate an alarm to alert the tool machine operator or to stop the machine automatically so that the tool can be replaced.

In accordance with various embodiments of the technique and apparatus of the invention, a single sensing means or a plurality of sensing means can be utilized in order to provide the desired measurements.

DESCRIPTION OF THE INVENTION

A more specific description of the invention is disclosed with reference to the accompanying drawings wherein FIG. 1 is a diagrammatic view of a milling machine which incorporates an embodiment of the invention;

Figures 1, 2:
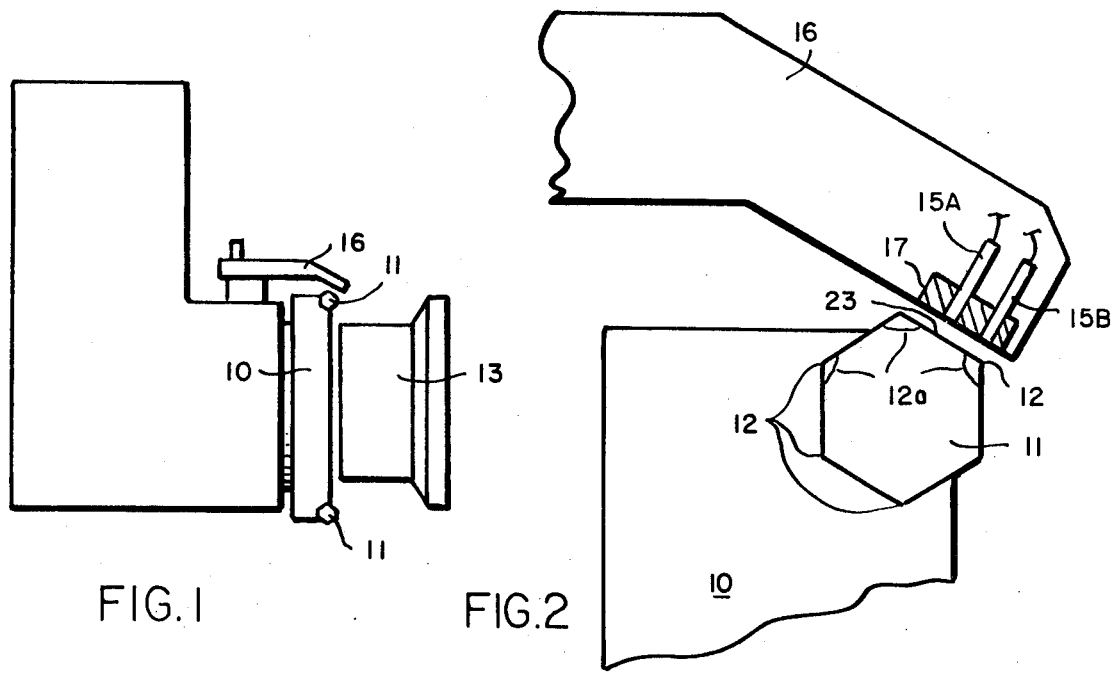
FIG. 2 is an enlarged view of a part of the machine of FIG. 1 showing a portion of the invention.

FIGS. 1 and 2 depict in diagrammatic form a milling machine using a system of the invention comprising a pair of sensing devices for determining the distances required for the tool wear detection. As shown therein, a milling machine comprises a rotary member 10 (a portion of which is enlarged and shown in FIG. 2) having a plurality of cutting tools 11, each with appropriate cutting surfaces 12, all mounted so as to provide cutting actions against a suitably mounted work piece 13. The rotary member rotates in a plane perpendicular to the paper, the specific structure of such a machine being well known to those in the art so that it need not be shown or described in any more detail here. For example, as shown enlarged in FIG. 2, each of the cutters 11 may have a plurality of cutting surfaces 12 thereon, as shown, so that as a particular cutting surface thereof wears in the regions 12A as shown, the cutting tool 11 can be rotated on member 10 so as to place an adjacent cutting surface in the correct position for a cutting operation. In this way, a cutting tool 11 does not have to be replaced each time a cutting surface becomes worn until all of the cutting surfaces 12 thereon are sufficiently worn to have reached the end of their useful lives.

A pair of sensing devices 15A and 15B are fixedly mounted near one end of a sensing arm 16 which is, for example, fixedly mounted to the frame of the machine in any appropriate manner, the devices being used to measure appropriate distances with reference to selected surfaces of the cutting tool and to provide output voltage signals representative thereof. The devices are shown as embedded at their sensing ends in an insert member 17 made of a suitable epoxy material. Such a structure appears helpful when using eddy current sensors, as discussed below, although embedding in epoxy is not absolutely necessary. The output voltage signals produced thereby are supplied to suitable sensing circuitry 18 (FIG. 3), which can be mounted, for convenience, on the sensing arm or which, if desired, could be mounted elsewhere. Such sensors may be, for example, of the eddy current electronic micrometer type which can measure distances from the end of the probe to a surface adjacent thereto by producing an output voltage representative thereof. Typical devices of such a nature may be of the type made and sold by Kaman Sciences Corporation of Colorado Springs, Colorado under the series model designation KD-2300. One such device which has been found useful has a diameter of 2 mm. and is designated as the model KD-2300-0.5SU.

A first sensor 15A is appropriately mounted so as to be directly over a non-wearing reference surface region of each of the tools as each tool moves past the region over which the sensors are located so that, at a particular point in time, the first sensor 15A is directly over the reference surface region 23. A second sensor 15B is appropriately mounted so as to be directly over the cutting, i.e., the wearing surface region 12 of the tool. Each sensor thereupon produces an output voltage signal which is proportional to the distance from the sensor to the surfaces opposite to which each is positioned.

Figure 4:
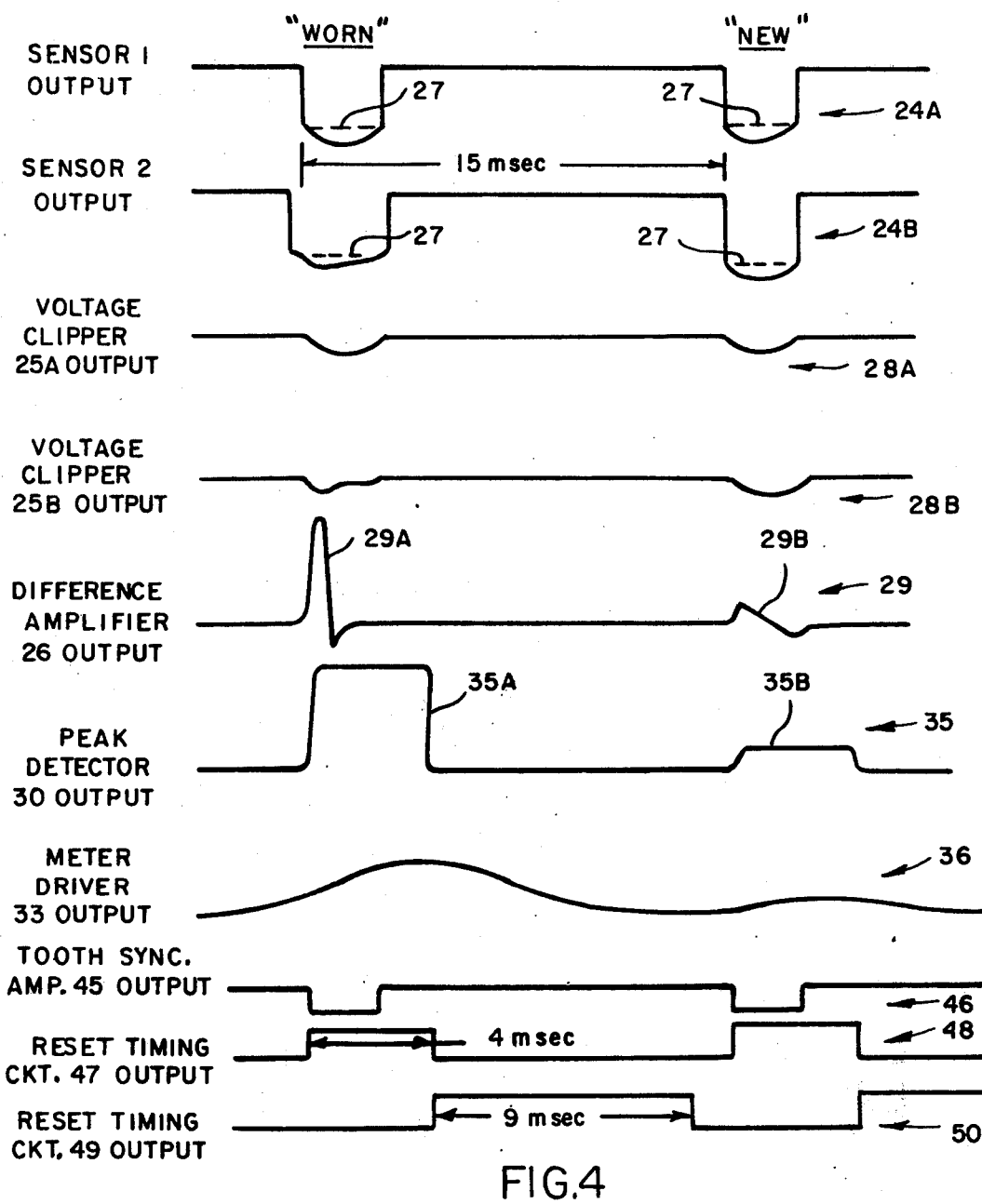
FIG. 4 shows various waveforms of signals present at specified points in the circuitry of FIG. 3.

The sensors can be adjusted for phasing so that they can be actuated simultaneously opposite the desired surfaces by appropriately positioning them with respect to each other in a plane substantially tangential to a circle which is concentric with the circle which describes the movement of the cutters. Once the sensors have been appropriately positioned on the arm 16, their sensing ends, if desired, can be immersed in an epoxy insert 17 in a manner well known to those in the art, although it is understood that the use of such insert is not essential. The output of the sensors 15A and 15B will be voltage signals 24A and 24B respectively, as shown in FIG. 4, which represent the distances from the sensing ends thereof to the reference non-wearing surface 23 and to the cutting surface 12, respectively. In FIG. 4, for illustrative purposes, the waveforms contain portions which result from measurements made with respect to two teeth, one tooth being in a "worn" condition and the other being in an essentially "new" condition, as shown at the top thereof.

Figure 3:
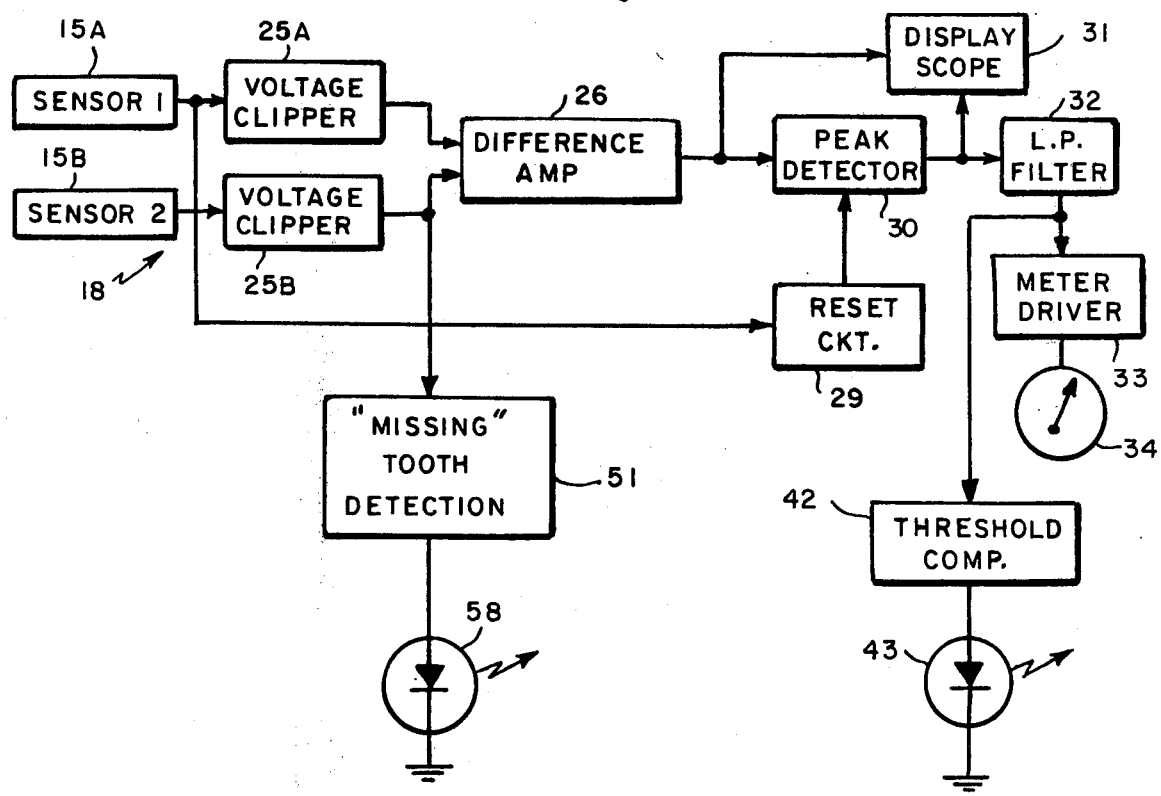
FIG. 3 is a block diagram of the circuitry representing one embodiment of the invention.

As can be seen in FIG. 3, the output voltage signals from each of the sensors are supplied to voltage clipping circuits 25A and 25B, respectively. The representative waveforms 24A and 24B of the signals from each of the sensors, as shown in FIG. 4, depict the effects of the different responses of each of the sensors which tends to cause the leading edges of the pulse signals therefrom to occur at different times, even though the sensors are arranged as closely as possible to provide simultaneous sensing of the cutting surface and the non-wearing reference surface. In order to overcome the problems associated with the different sensor responses, the voltage signals 24A and 24B are supplied to the voltage clipping circuits which operate to clip the signals at an appropriate fixed level 27 and pass only those portions 28A and 28B, respectively, of the signals above such threshold clipping level. After passing through the clipping circuits, the clipped signals are supplied to a difference amplifier circuit 26, having a suitable gain, which measures the voltage difference therebetween and amplifies such voltage difference. The output from the difference amplifier, which represents the amplitude differences of the clipped signals from the sensors, is shown by waveforms 29 in FIG. 4 for a typical amplifier gain of approximately 10, for example.

As can be seen in FIG. 4, for a "worn" tooth condition, for example, the amplified difference has a substantially higher peak amplitude, as represented by the difference 29A, while a "new" tooth condition produces a signal with a much lower peak amplitude, as represented by the difference signal 29B. The amplified difference signals are then passed through a peak detector circuit 30 to produce waveforms 35 as shown in FIG. 4. The output of the difference amplifier 26 (and/or the output of the peak detector 30) may be appropriately supplied to a suitable display device 31, such as an oscilloscope which utilizes appropriate synchronizing signals having a synchronized relationship to the rotation of the milling tool. Alternatively, the output of the peak detector may be supplied through a low pass filter 32 to an output indicator 34 in the form of a meter, for example, via a suitable meter drive circuit 33 which produces waveform 36 as shown in FIG. 4.

Figure 5:
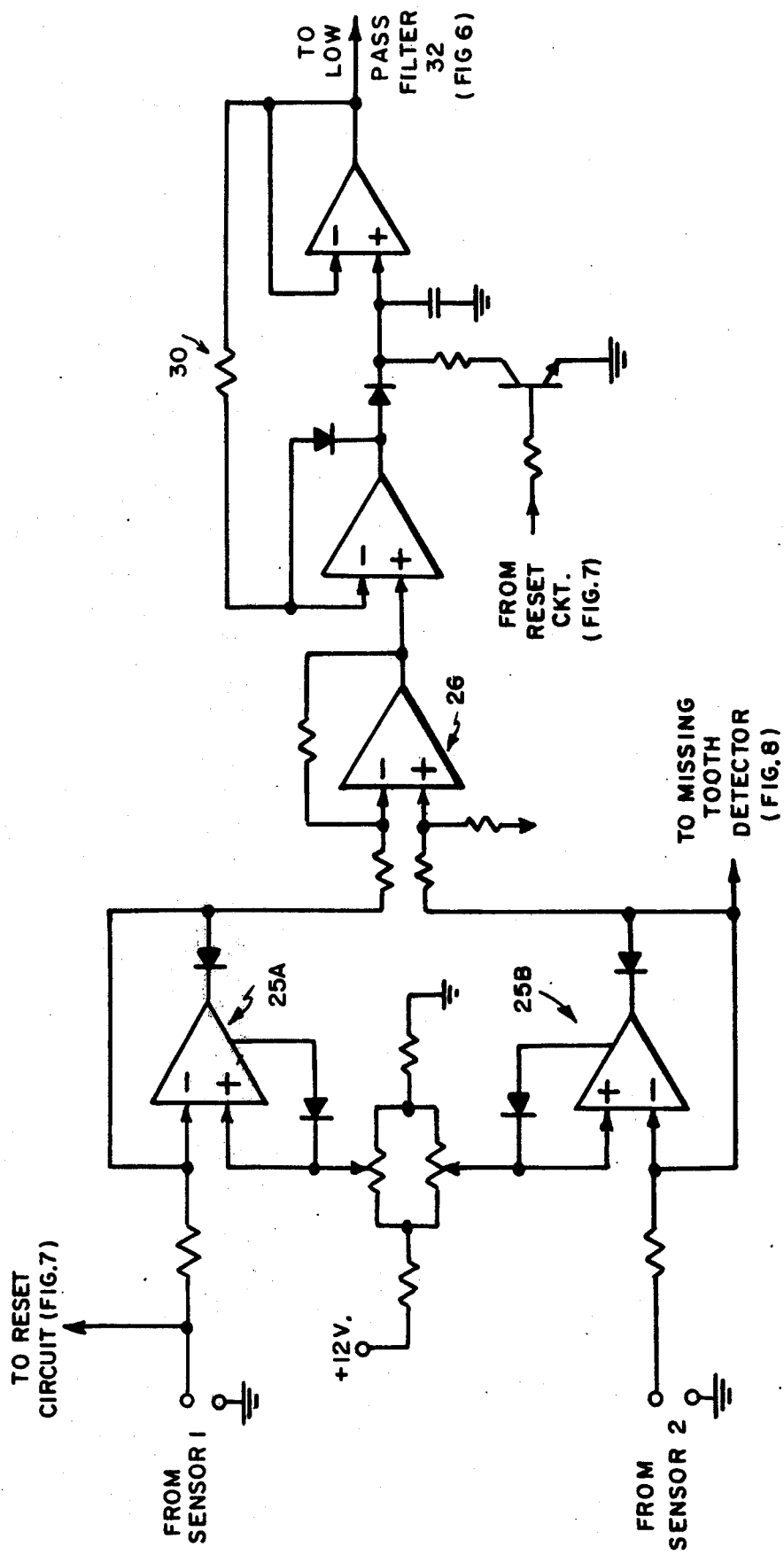
FIGS. 5 to 8 show more detailed schematic diagrams of portions of the embodiment of FIG. 4.

FIGS. 5-8 show in more detail the circuitry of FIG. 3. FIG. 5 depicts the voltage clipping circuits 25A and 25B, the difference amplifier 26 and the peak detector circuit 30. As seen therein, the output voltages from sensors 1 and 2 are applied to operational amplifiers which together with the diode circuitry associated therewith provide the clipper output voltages 28A and 28B as shown in FIG. 4, which latter voltages are supplied to differential amplifier circuit 26. The latter circuit produces an output signal, such as shown by waveforms 29A for worn teeth and 29B for new teeth which represents the effective difference between waveforms 28A and 28B, which difference signal is appropriately amplified, as shown in FIG. 4.

Figure 6:
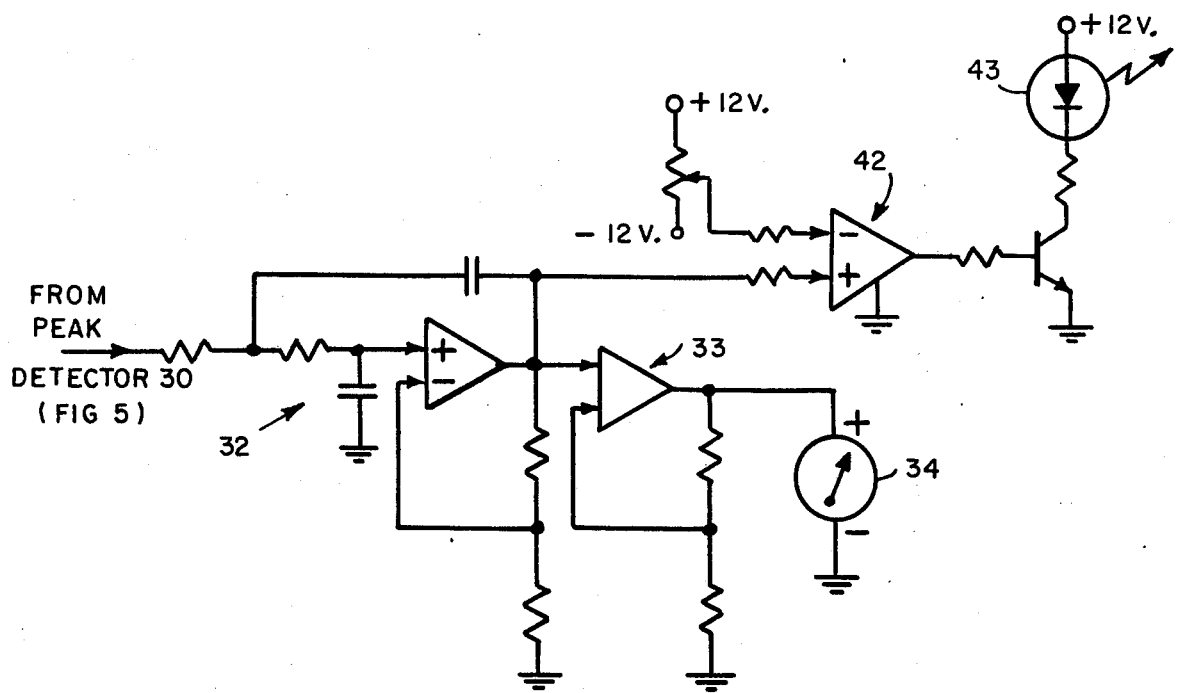

The peak detector circuitry 30, provides in effect a sample and hold function which produces a voltage pulse, such as shown by pulses 35A and 35B, for example, the amplitudes of which are substantially equal to the maximum amplitudes of waveforms 29A and 29B, respectively, for example. In order to provide a sensory indication (i.e. an audible or visual indication) that a tooth has become sufficiently worn to require replacement, the peak-detected output is supplied to a low pass filter circuit 32 which, as shown in FIG. 6, is, for example, a conventional two-pole Butterworth active filter with a suitably selected cut-off frequency to remove rapid variations in the signal due to the passage of individual teeth by the sensors. The filter circuit averages the peak detector output and provides a signal 36 (FIG. 4) which effectively represents the overall tooth wear for the entire milling tool (i.e., the average wear for all the teeth). Such signal is appropriately used to drive a meter 34 via a meter buffer driver amplifier 33.

Alternatively, the low pass filter output signal may be compared with a reference voltage at a threshold comparator circuit 42 so that when the amplitude of average signal associated with a particular cutting tool exceeds a preselected level a suitable visual device, such as a light-emitting-diode 43 (L.E.D.), is activated.

Figure 10:
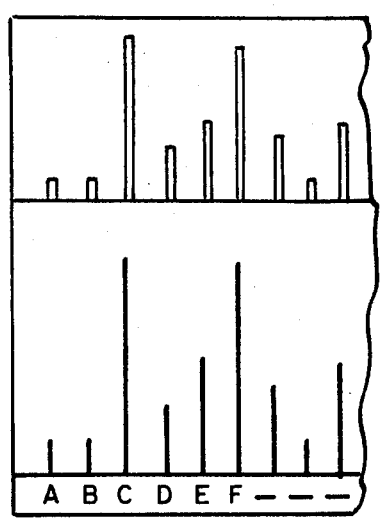
FIG. 10 shows a portion of an exemplary oscilloscope display of specified signals of the circuit of the invention with reference to a plurality of tools which are being monitored.

In a further alternative, as previously mentioned, the outputs from the difference amplifier 26 and the peak detector 30 can be examined on an oscilloscope which, when appropriately synchronized with the signals from the sensors, provides a display of such signals. For example, to provide a fixed phase reference to trigger the scope at the same point in the mill revolution a coil can be mounted adjacent the rotary mill head and a small magnet mounted on the mill head which induces an electrical pulse in the coil once per revolution as it passes the coil. Such pulse can be used to trigger the oscilloscope via the "external trigger" input thereof. Individual tooth signals can be examined in detail by using the delayed sweep feature of a conventionally available oscilloscope as would be well known to the art. A typical display, for example, for a milling machine having a plurality of cutting tools is partially shown in FIG. 10. As can be seen therein, in the lower region thereof, the amplified difference signals at the output of amplifier 26 for each of the cutting tools are displayed, while the outputs of the peak detector 30 associated with each of said difference signals are displayed in the upper region thereof. Exemplary signals relative to six cutting surfaces, identified as cutting surfaces A, B, C, D, E and F in the display, are discussed specifically to show and describe the condition of the cutting tools which they represent. Thus, cutting tools A and B may be described as having a general condition comparable to that of relatively new tools, i.e., the difference signals are relatively low, showing that the cutting surface has not worn to any degree. The cutting surface for tool C is seen to have had relatively heavy wear and in an actual milling machine, with respect to which the display shown herein was taken, such tool was shown upon inspection to be well worn and slightly chipped. Cutting tool D is shown to have relatively light wear, cutting tool E might be termed as having medium wear, while tool F is determined to have relatively high wear or a badly chipped surface.

The display shown therein for a typical milling machine was made with sensors having calibration sensitivities of 50 millivolts per 0.001 inches, with a gain of 10 in the difference amplifier 26 to produce a difference voltage sensitivity of 500 millivolts per 0.001 inches. A physical check was made of each tool of an actual machine in which the system of the invention was used, utilizing appropriate mechanical measuring devices, such as dial indicators, to determine the reliability of the system of the invention. It was determined that a relatively good correspondence occurred between the mechanical measurement made when the machine was not in operation and the measurements made with the system of the invention when the machine was in operation. A chart showing exemplary measurements made by a dial indicator, for example, as compared with measurements made by the invention, is shown below for the exemplary six tools as discussed above with reference to FIG. 10.

| Cutting Tool | Distance Measurement by Invention | | | Distance Measured by Dial Indicator |
| --- | --- | --- | --- | --- |
| | Oscilloscope (cm) | Volts | (Thousandths of Inches) | (Thousandths of Inches) |
| A | 0 | 0 | 0 | −0.2 |
| B | 0 | 0 | 0 | −0.5 |
| C | 2.1 | 4.2 | 8.4 | 8.1 |
| D | 0.4 | 0.8 | 1.6 | 0.5 |
| E | 0.9 | 1.8 | 3.6 | 3.6 |
| F | 2.0 | 4.0 | 8.0 | 7.8 |

As can be seen, the indicated wear as determined by the system of the invention was relatively close to that provided by mechanical measurements. While there may be some slight drifts in the measurements due to changes in the physical alignment of the sensors with the tool or due to temperature effects on electronic circuit drifts, such changes would appear to be acceptable for many production line applications. Should further compensation for temperature changes be desired, or required, in particular applications, standard temperature compensation techniques well-known in the art for such electronic micrometers can be used.

Figure 7:
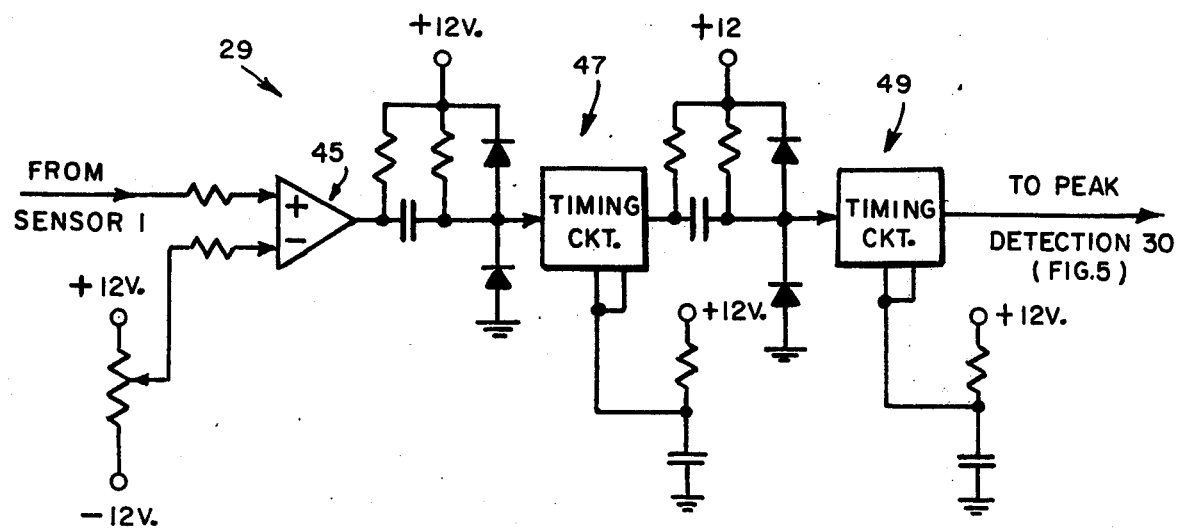
Figure 8:
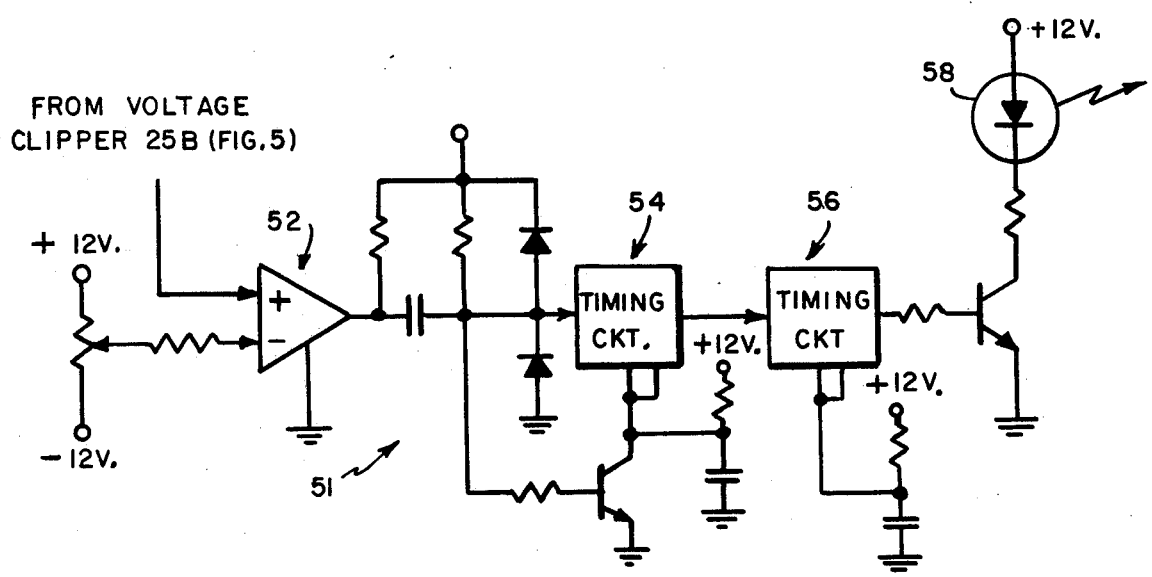

In the operation of the peak detector circuitry 30 the pulses from difference amplifier 26 are in effect "stretched" so that the peak value of the difference signal is weighted heavily in the averaging process of the low pass filter 32. The peak detector output follows the input so long as the input voltage is rising, while if such voltage falls the peak voltage attained is held until the peak detector is reset to zero by an auxiliary reset signal from reset circuit 29. Such reset circuit is shown in FIG. 7 wherein the reset signal is derived from the unclipped signal from sensor 1. A tooth synchronizing-amplifier 45 produces a negative-going transition every time the output from sensor 1 exceeds a pre-selected threshold reference voltage level, the latter level being set so that the next stage is triggered when the leading edge of the tooth starts to pass sensor 1, as seen by waveform 46 of FIG. 4. After a reset pulse delay of a fixed time period (e.g. 4 milliseconds in a typical embodiment for a machine with teeth which pass a fixed point approximately every 15 milliseconds) in pulse delay circuit 47, the output of which is depicted as waveform 48 of FIG. 4, a reset pulse timer circuit 49 produces a reset pulse, shown as waveform 50 in FIG. 4, which resets the peak detector to zero for a pre-selected fixed time period (e.g. 9 milliseconds in a typical embodiment), after which the peak detector is released so that it can follow the next tooth signal which in a typical embodiment may be about 1.7 milliseconds later, for example.

Figure 9:
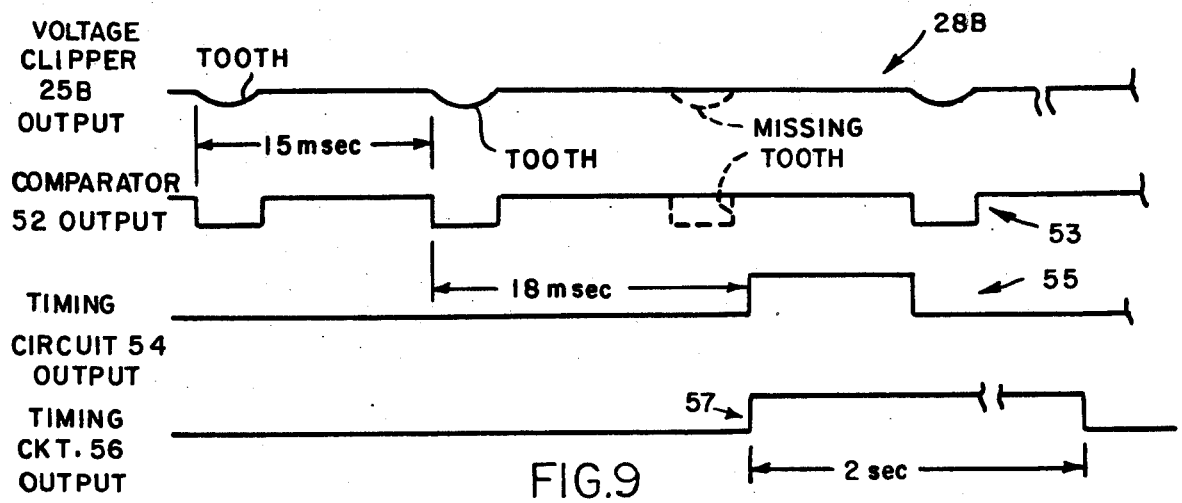
FIG. 9 shows various waveforms of signals present at specified points in the circuitry of FIG. 8.

Even though the average tooth wear of a particular mill head is within acceptable limits, a particular tooth in such head may have worn severely or may have been chipped or otherwise broken off and is, therefore, in effect "missing" with respect to the cutting operation. A missing tooth detection circuit 51 can be used as shown generally in FIG. 3 and, more specifically, in FIG. 8. In the latter figure the output signal from voltage clipping circuit 25B (shown as waveform 28B both in FIG. 4 and in FIG. 9) representing the clipped voltage of the wearing surface of a tooth as obtained from sensor 2 is compared to an adjustable threshold voltage at comparator 52 to produce a pulsed waveform 53 as shown in FIG. 9 which is supplied to timing circuitry 54. So long as the clipped voltage periodically exceeds the threshold voltage, the timing circuit maintains timing circuit 54 in a reset condition so that no output occurs therefrom. If the clipped voltage fails to exceed the threshold due to excessive wear or a chipped condition, or such tooth is otherwise missing, the timing circuit 54 generates a pulse lasting until detection of the next tooth, as shown by waveform 55 in FIG. 9 which shows a typical pulse duration of 10 milliseconds, for example. Such pulse is thereupon supplied to a further pulse timing circuit 56 which in effect further stretches the pulse to a relatively long duration as long as 2 seconds, for example, as shown by waveform 57 in FIG. 9. The latter signal is used to activate a visual indicator, such as L.E.D. indicator 58. Thus, if a mill head has one or more missing teeth the L.E.D. would appear to remain continuously activated, to indicate such condition.

Figure 11:
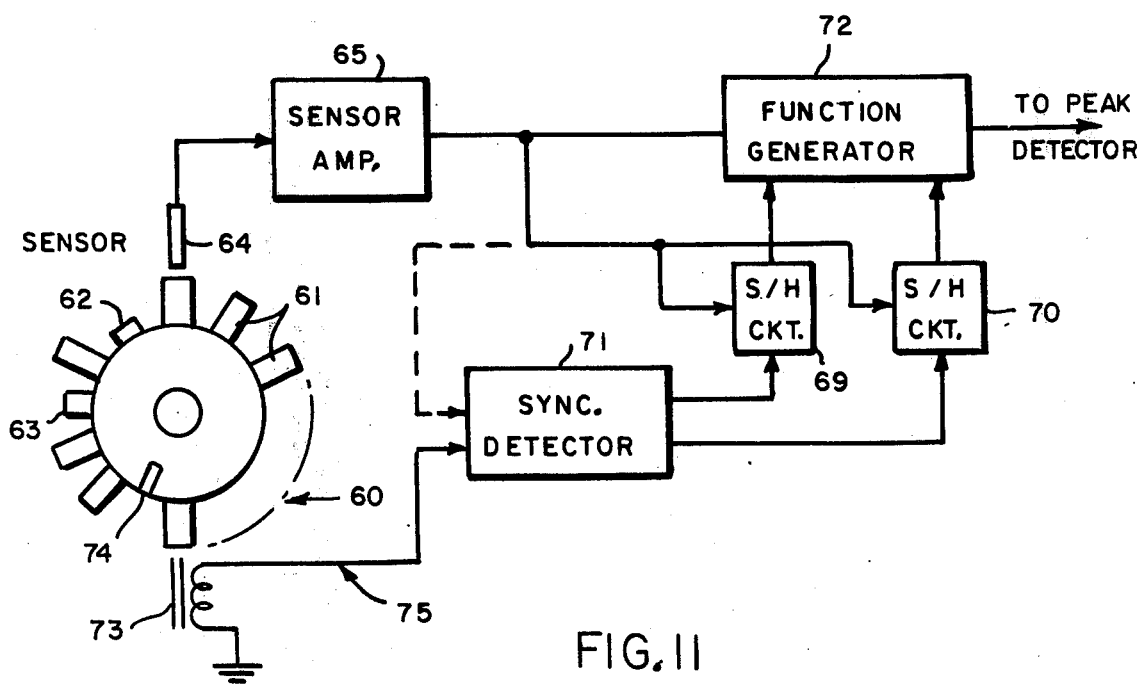
FIG. 11 is a diagrammatic view of an alternative embodiment of the invention.

An alternative method for measuring tool wear in accordance with the invention can be performed by using only a single sensor in order to save the cost of using two such sensors, the processing of the signals therefrom requiring somewhat different circuitry prior to the peak detection operation that that required for the dual sensor system described above. As can be seen in FIG. 11, a rotary milling machine member 60 having a plurality of cutters 61 mounted thereon has one or more intermediate reference elements such as elements 62 and 63 mounted between selected ones of the cutters, as discussed below. Each of the reference elements projects a selected reference height from the surface of the tool body and, accordingly, is at a known reference distance from a sensor 64 mounted at a pre-selected location relative to the mill tool. The reference surface of each element is low enough to be below the minimum expected wear height of the cutting tools 61 and high enough to be within the measurement range of the sensor.

If the relative locations of the sensor 64 and the cutting and reference surfaces remained fixed over the course of time during which such a system operates, only a single reference surface need be used and all of the distances from the sensor to the cutting surfaces could be appropriately compared to the reference distance to such a single reference surface in order to determine tool wear. However, as discussed above, temperature, vibrations and sensor drift characteristics, for example, may tend to vary the location of the single sensor relative to the mill tool and to alter the sensor output vs. distance characteristics in a relatively slow manner, i.e., such variations tend to occur over time periods relatively long compared to the time period of rotation of the mill tool. It may be necessary, therefore, to take such variations into account in the measurement of tool wear using a single sensor, while such variations are automatically taken into account in the dual sensor system. One technique for doing so in the single sensor case is shown in FIG. 11.

Figure 12:
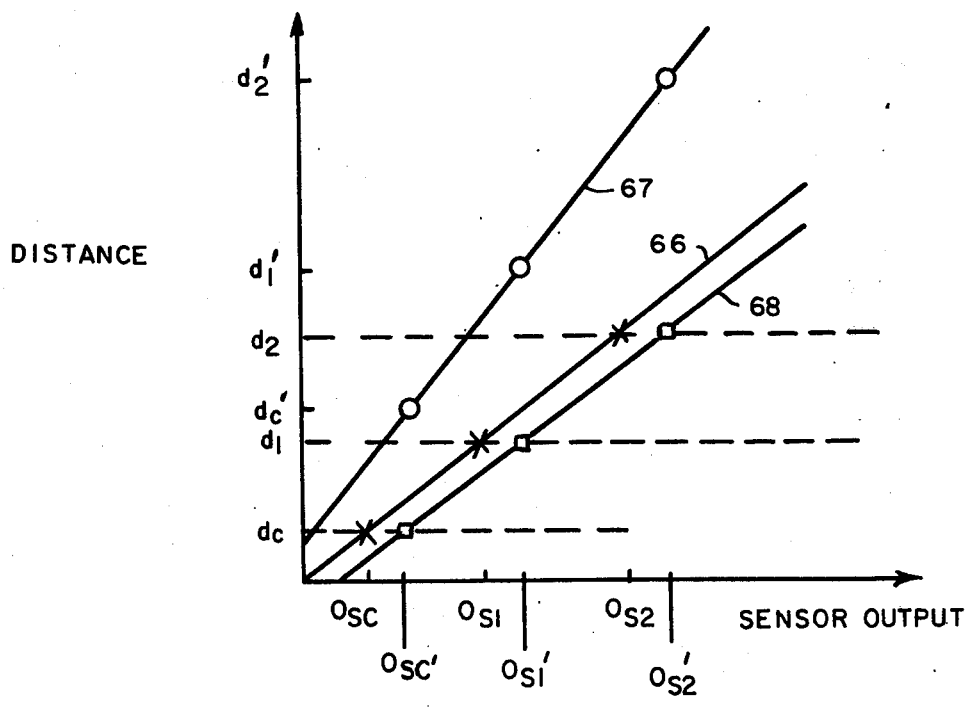
FIG. 12 is a graphical representation of distance vs. sensor output characteristics helpful in understanding the operation of the embodiment of FIG. 11.

As seen therein, the output of the sensor 64 is appropriately amplified by sensor amplifier 65. The two reference elements of the mill tool have different heights $h_1$ and $h_2$ from the tool body and, hence, their surfaces are at different distances $d_1$ and $d_2$ from the sensor. The graph of FIG. 12 shows a curve 66, for example, which represents the relationship between the sensor signal output amplitudes $O_{S1}$ and $O_{S2}$ and the distances $d_1$ and $d_2$, respectively, for a typical sensor of the type discussed above. Thus, sensor output signal $O_{S1}$ corresponds to the distance $d_1$ and sensor output signal $O_{S2}$ corresponds to the distance $d_2$.

If the sensor characteristics and the location of the sensor relative to the mill tool remains the same, the sensor measurement of the distance $d_c$ to a cutting tool is accurately represented by the sensor output $O_{Sc}$. If, however, the sensor characteristics change, as shown by curve 67 of FIG. 11, wherein both a change in slope and a zero offset are introduced, due to movement of the sensor relative to the tool as well as changes in the sensor characteristics, the sensor output $O'_{Sc}$ with respect to the cutting surface would represent a distance $d'_c$ which measurement, by causing the cutting surface to appear farther away from the sensor, would make the cutting surface appear to be in a more worn condition than it is.

It is necessary, therefore, to provide a means for correcting for the error introduced by such variations in order that a true representation of cutting surface wear can be obtained. Such correction can be demonstrated graphically in FIG. 12 as follows. In accordance with such correction, the measured sensor outputs with respect to each of the reference elements $O'_{S1}$ and $O'_{S2}$ are used to generate a curve of the type shown by curve 68 of FIG. 11, i.e., the values of $O'_{S1}$ and $O'_{S2}$ are assumed to correspond to the initial known reference distances $d_1$ and $d_2$. The sensor output $O'_{Sc}$ then represents the desired distance $d_c$ from the sensor to the tool cutting surface in accordance with curve 68, the effects of variations in sensor characteristics having been removed. The generation of a distance vs. sensor output characteristic in accordance with curve 68 can be performed with a suitable function generator of the type well known to those in the art, as discussed below.

For this purpose the sensor outputs at the times when the sensor is opposite the reference surfaces 62 and 63 are supplied to sample and hold circuits 69 and 70, the operation of the latter being appropriately synchronized by synchronous detection circuitry 71 so that the sample and hold outputs represent the sensor outputs $O'_{S1}$ and $O'_{S2}$ for example. The outputs from sample and hold circuits 69 and 71 are supplied to a function generator 72 which, from the values so obtained and the known values $d_1$ and $d_2$, produces an output signal which is a linear function of an input signal in accordance with such values as represented by curve 68, for example. An input signal to function generator 72 from sensor amplifier 65 thereupon produces an output signal from the function generator in accordance with such linear function. Thus, a sensor amplifier output as represented by the signal $O'_{Sc}$, for example, in FIG. 12, produces an output representative of the distance $d_c$ as desired. If the sensor environmental characteristics do not change, curve 68 effectively coincides with curve 66.

Each of the output signals from the function generator, as thereby corrected to take into account the above undesired variations, represents the distance from the sensor to each of the cutting surfaces of the tool and such corrected signals can be used directly as a measure of the wear characteristics thereof. Accordingly such signals are supplied to a peak detector, such as peak detector 30 in FIG. 1, for subsequent processing and display in substantially the same manner discussed above with reference to the dual-sensor system.

In order to synchronize the operation of the sample and hold detectors of FIG. 11 with the rotational motion of the mill tool, the synchronizing signal to the synchronous detector can be supplied from a synchronizing sensing coil 73 mounted adjacent the mill tool but sufficiently remote from the sensor 64 to prevent interference. A small permanent magnet 74 is attached to the tool 60 at a known position relative to the reference surfaces 62 and 63 so that a timing pulse occurs at the coil wherever the magnet passes by. The coil output pulse is used as a known phase reference signal to operate the synchronous detector circuit 71 so that sample and hold enable signals are supplied to the sample and hold circuits from synchronous detector 71 at the correct times relative to the phase reference signal from coil 73.

Alternatively, the coil/magnet combination and the connecting lead 75 therefrom to synchronous detector 71 can be omitted and synchronism obtained by placing the reference surfaces in an asymmetrical pattern, as by placing one reference surface in an intermediate position between two adjacent cutters, omitting the second reference surface from the next intermediate position and then placing the second reference surface in the next intermediate position (forming a pattern R-B-R, where R represents a reference surface and B represents a blank space). Recognition by the synchronous detector 71 of such a coded pattern at the output of sensor 65 via a suitable correction shown by dashed line 75 would provide sufficient phase reference information to permit the generation of sample and hold enable pulses at the desired times.

Tool wear measurements made in accordance with embodiments discussed above permits the dynamic measurement thereof in real time in a direct way, i.e., where a direct measurement of the erosion of the tool cutting surface is made without the need for an indirect, inferential measurement of another tool characteristic when the latter measurement leads to the inferential errors which normally arise in such systems. The measurement is relatively accurate and linear and achieves relatively long term stability. Moreover, the implementation thereof can be achieved at relatively low cost. The system permits a variety of display formats and signal processing techniques for whatever desirable use may be required of the system in various applications, and the system is generally not sensitive to variations in tool dimensions due to temperature, or other effects thereon.

The use thereof tends to reduce the wasted production time due to the down time which occurs because of broken or excessively worn tools and tools can be more effectively used for their overall useful life without being changed prematurely or at a time which is too late to save the work pieces which are produced when the tool has gone beyond the useful life.

What is claimed is:

1. A system for detecting the wear characteristics of at least one cutting tool having at least one cutting surface and at least one non-wearing reference surface, said system comprising
    at least one sensing means for providing information concerning the distance from said sensing means to said at least one cutting surface and for providing information concerning the distance from said sensing means to said at least one non-wearing reference surface;
    means for processing the information concerning said at least one cutting surface distance and the information concerning said at least one reference surface distance, said processing means providing a determination of the wear characteristics of said at least one cutting tool.

2. A system in accordance with claim 1 wherein said at least one sensing means comprises at least one electronic sensing means for providing at least one first signal having an amplitude representing said at least one cutting surface distance and at least one second signal having an amplitude representing said at least one reference distance; and said processing means includes means responsive to the amplitudes of said at least one first signal and said at least one second signal for producing an output signal representing the wear characteristics of said at least one cutting tool; and means responsive to said output signal for providing a sensory indication when said output signal exceeds a predetermined level.

3. A system in accordance with claim 2 wherein said sensing means comprises two electronic sensors, a first one of said sensors, mounted so as to be adjacent said at least one cutting surface as said cutting tool passes by, for providing said at least one first signal and a second one of said sensors, fixedly mounted with respect to said first sensor so as to be adjacent said at least one non-wearing reference surface when said first sensor is adjacent said at least one cutting surface, for providing said at least one second signal; and said output signal producing means includes means for comparing the amplitudes of said at least one first signal and said at least one second signal.

4. A system in accordance with claim 3 wherein said comparing means includes
   means for providing a signal representing the difference in amplitudes of said first and second signals; and
   means for detecting the peak of said amplitude difference signal to produce said output signal.

5. A system in accordance with claim 4 wherein
   said peak detecting means operates so that the level of said output signal is maintained at the peak level of said amplitude difference signal; and
   further wherein said processing means includes means for resetting the level of said output signal to zero after a preselected time interval following the detection of said peak level by said peak detecting means.

6. A system in accordance with claim 3 wherein said system detects the wear characteristics of a plurality of cutting tools, each having a cutting surface and an associated non-wearing reference surface, said sensors being mounted so as to be simultaneously adjacent the cutting surfaces and corresponding reference surfaces of successive ones of said cutting tools as they pass by, whereby a plurality of successive output signals representing the wear characteristics of each of said cutting tools is produced.

7. A system in accordance with claim 6 wherein said sensory indication providing means comprises an oscilloscope display means responsive to said successive output signals produced with respect to each of said cutting tools for visually displaying the wear characteristics of each of said cutting tools.

8. A system in accordance with claim 6 and further including
   means for detecting the absence of one or more of said plurality of cutting surfaces.

9. A system in accordance with claim 2 wherein said electronic sensing means includes at least one eddy-current sensor means.

10. A system in accordance with claim 1 wherein said sensing means comprises a single electronic sensor, mounted so as to be successively adjacent said at least one non-wearing reference surface and said at least one cutting surface as said cutting tool passes by, for successively providing at least one reference surface signal representing said at least one reference surface distance and at least one cutting surface signal representing said at least one cutting surface distance.

11. A system in accordance with claim 10 wherein said processing means is responsive to said at least one reference surface signal and to said at least one cutting surface signal to provide a cutting distance signal which represents the distance from said sensor to said at least one cutting surface, said processing means including
   means for correcting the level of said cutting distance signal to take into account errors arising with respect to the signals produced by said sensor.

12. A system in accordance with claim 11 and further including means for synchronizing the supplying of said at least one reference surface signal and said at least one cutting surface signal to said correcting means.

13. A system in accordance with claim 12 wherein said synchronizing means includes
   timing means for providing a timing signal having predetermined timed relationships with the provision by said sensor of said at least one reference surface signal; and
   means responsive to said timing signal for controllably timing the supply of said at least one reference surface signal to said correcting means.

14. A system in accordance with claim 11 wherein said processing means further includes
   means for detecting the peak of said cutting distance signal to produce said output signal.

15. A system in accordance with claim 14 wherein
   said peak detecting means operates so that the level of said output signal is maintained at the peak level of said cutting distance signal; and
   further wherein said processing means includes means for resetting the level of said output signal to zero after a preselected time interval following the detection of said peak level by said peak detecting means.

16. A system in accordance with claim 10 wherein said system detects the wear characteristics of tool members comprising at least one cutting surface and at least two nonwearing reference surfaces;
   said sensing means providing at least two reference surface signals and at least one cutting surface signal, and further wherein said correcting means comprises
   function generator means responsive to said at least two reference signals for providing an output signal which is a substantially linear function of the input signal thereto, said linear function being determined by the values of said at least two reference surface signals and said input signal being said at least one cutting surface signal whereby said output signal represents the distance from said sensor to said at least one cutting surface.

17. A system in accordance with claim 16 wherein said cutting tool includes a plurality of cutting surfaces and said sensing means provides a plurality of successive cutting surface signals as input signals to said function generator means for producing a plurality of successive output signals representing the distances from said sensing means to said plurality of cutting surfaces.

18. A system in accordance with claim 17 and further including means for synchronizing the supplying of said at least two reference surface signals and said plurality of cutting surface signals to said function generator means.

19. A system in accordance with claim 18 wherein said synchronizing means includes
   timing signal means for providing a timing signal having a predetermined timed relationship with the provision by said sensor of said at least two reference surface signals; and
   means responsive to said timing signal for controllably timing the supply of said reference signals to said function generator means.

20. A system in accordance with claim 19 wherein said controllable timing means includes
   at least two sample and hold circuits responsive to said at least two reference surface signals; and
   synchronous detector means responsive to said timing signal for providing control signals for controlling the operation of said sample and hold circuits to synchronize the supplying of said reference surface signals and said plurality of cutting surface signals to said function generator means.

21. A system in accordance with claim 20 wherein said timing signal means includes magnetic means positioned on said cutting tool at a predetermined spatial relationship relative to said reference surfaces; and pick-up means mounted adjacent said cutting tool and responsive to the presence of said magnetic means for providing said timing signal when said magnetic means passes thereby.

22. A system in accordance with claim 18 wherein said reference surfaces are positioned in a coded pattern on said cutting tool, said sensor providing a corresponding coded pattern of said reference surface signals; and said synchronizing means includes means responsive to said reference surface signals and capable of recognizing said coded pattern thereof for producing control signals for controlling the supplying of said reference surface signals to said function generator means.

23. A system in accordance with claim 17 and further including means for detecting the absence of one or more of said plurality of cutting surfaces.

* * * * *